United States Patent
Grant et al.

(10) Patent No.: US 9,050,384 B2
(45) Date of Patent: Jun. 9, 2015

(54) MEANS OF APPLYING PERACETIC ACID TO ACHIEVE ENHANCED MICROBIAL EFFECT

(71) Applicants: Austin Grant Inc., Apopka, FL (US); GroupAg LLC, Rexburg, ID (US)

(72) Inventors: Lucie Grant, Apopka, FL (US); Kent Wasden, Rexburg, ID (US)

(73) Assignees: Austin Grant Inc., Apopka, FL (US); GroupAg LLC, Rexburg, ID (US)

( * ) Notice: Subject to any disclaimer, the term of this patent is extended or adjusted under 35 U.S.C. 154(b) by 108 days.

(21) Appl. No.: 13/856,378

(22) Filed: Apr. 3, 2013

(65) Prior Publication Data

US 2014/0301894 A1   Oct. 9, 2014

(51) Int. Cl.
| | | |
|---|---|---|
| *A61L 9/00* | (2006.01) | |
| *A62B 7/08* | (2006.01) | |
| *A61L 2/20* | (2006.01) | |
| *A23L 3/3445* | (2006.01) | |
| *A23B 7/152* | (2006.01) | |

(52) U.S. Cl.
CPC .................. *A61L 2/20* (2013.01); *A23L 3/3445* (2013.01); *A23B 7/152* (2013.01)

(58) Field of Classification Search
CPC ........... A61L 2/00; A61L 2/186; A61L 2/208; A61L 2/22; A61L 9/015
USPC ............ 422/1, 28, 32, 34, 125, 298, 305–307
See application file for complete search history.

(56) References Cited

U.S. PATENT DOCUMENTS

2010/0196197 A1 *   8/2010   Rovison et al. ................ 422/28
2012/0189494 A1     7/2012   Rovison, Jr. et al.

OTHER PUBLICATIONS

F.P.Greenspan, M.A. Johnsen, and P.C. Trexler, Peracetic acid aerosols, Chem. Specialties Mfrs. Assoc. Proc. Ann. Meeting, 1955, 42:59-64.
D.M. Portner, R.K. Hoffman, Sporicidal Effect of Peracetic Acid Vapor, App. Microbiology, 1968, 16:1782-1785.

* cited by examiner

*Primary Examiner* — Monzer R Chorbaji
(74) *Attorney, Agent, or Firm* — William Lovin & Assoc. LLC

(57) ABSTRACT

The present method relates to a novel means of safely applying peracetic acid (peroxyacetic acid or PAA) to inert solid surfaces and non-inert surfaces such as those found on various agricultural products including citrus fruit, pome fruit, potatoes, and vegetables to achieve an enhanced microbial effect. This is useful as a low cost means of sanitizing agricultural products in situ in the storage facility while simultaneously sanitizing the storage facility itself.

7 Claims, No Drawings

MEANS OF APPLYING PERACETIC ACID TO ACHIEVE ENHANCED MICROBIAL EFFECT

CROSS-REFERENCE TO RELATED APPLICATIONS

This application claims benefit of U.S. Provisional Patent No. 61/619,894 ("An Improved Means of Applying Peracetic Acid to Achieve Enhanced Microbial Effect") filed Apr. 3, 2012 which is incorporated herein by reference.

FIELD OF THE INVENTION

The present method relates to a novel means of safely applying peracetic acid (peroxyacetic acid or PAA) to inert solid surfaces and non-inert surfaces such as those found on various agricultural products including citrus fruit, pome fruit, potatoes, and vegetables to achieve an enhanced microbial effect. This is useful as a low cost means of sanitizing agricultural products in situ in the storage facility while simultaneously sanitizing the storage facility itself.

BACKGROUND OF THE INVENTION

For many years it has been known that peroxyacetic acid in various aqueous forms serves as a powerful antimicrobial agent. See, e.g., F. P. Greenspan, M. A. Johnsen, and P. C. Trexler. *Peracetic acid aerosols,* Chem. Specialties Mfrs. Assoc. Proc. Ann. Meeting, 42:59-64 (1955) and D. M. Portner and R. K. Hoffman, *Sporicidal Effect of Peracetic Acid Vapor,* App. Microbiology, 16:1782-1785 (1968). As a result, peroxyacetic acid is widely used in sanitization applications including those involving agricultural storage facilities and processing equipment. The present application discloses a new method of using PAA in these agricultural settings.

Specifically, in California and other citrus production areas, early season navel and mandarin oranges are harvested and treated with ethylene gas for two or more days in humidified "degreening" rooms at 20° C. to accelerate the degradation of residual chlorophyll to enhance the orange color of the fruit rind. Unsurprisingly, these environmental conditions are optimal for the development of green mold (*Penicillium digitatum*) and blue mold (*Penicillium italicum*). As a result, post-harvest "bin drenching" with commercial fungicides such as thiabendazole or imazalil is widely used to prevent the development of these pathogens. A predictable consequence of this practice is that fungicide resistant strains of mold develop and contaminate the associated degreening rooms, storage facilities, and packing equipment.

As a result, periodic prophylactic disinfection of empty storage rooms and processing equipment by means of antibacterial fog or mist is a routine occurrence. Formalin solution, which contains formaldehyde as an active ingredient, has long been used for this purpose. Unfortunately, formaldehyde is injurious to the fruit that it comes in contact with and thus may be used only twice yearly when the storage rooms are ordinarily empty. Further, many such storage rooms are never completely empty and are thus unavailable for sanitization by this means. Also, the maximum permissible amount of formaldehyde sanitizer allowed declines progressively as the proximity of inhabited dwellings or schools increases. As a result, other agents including peroxyacetic acid are increasingly used to disinfect such facilities and machinery. But this "two step" approach for separately disinfecting products and facilities is extremely time consuming and expensive. What is needed therefore is a method of using peroxyacetic acid alone to disinfect both the product and the facility in which it is stored and processed. Unfortunately, while various methods of using peroxyacetic acid vapors and/or fogs and/or mists are described in the prior art none are suitable for this purpose.

For example, U.S. Pat. Pub. No. 2010/0196197 discusses injecting peroxyacetic acid in a concentration ranging from 4,000 PPM to 10,000 PPM into a "heated gas stream" comprised of "sterile air" and/or other gases heated to a temperature "above about 250° C." The resulting heated vapor is then applied at a temperature ranging between, "about 80° C. and about 120° C." to, "metal, plastics, polymers, and elastomers" for a period of time ranging between, "15 and about 40 minutes." More recently, U.S. Pat. Pub. No. 2012/0189494 further refines this method for use in the context of heat sensitive polyethylene terephthalate (PET) bottles by disclosing a method in which the application temperature is lowered considerably to a range between, "about 57° C. and about 75° C." and the amount of time the vapor is actually applied ranges as low as, "5 seconds."

While these approaches may be useful for sterilizing inert, solid surfaces they are unsuitable for use on delicate organic surfaces such as those found on agricultural products. This is because the surfaces found on agricultural products are relatively rough compared to most inert, solid surfaces and the treatment times necessary to destroy pathogens must be greatly increased. Unfortunately, because of the relatively high application temperatures, increasing the treatment time has the unwanted side effect of damaging the agricultural product. Further, the methods discussed above require a source of sterile air or a source of some other sterile gas and as such both are unsuitable for use in the field where sterile compressed air or other gases may be unavailable.

Clearly, a method of generating and applying peroxyacetic acid vapor at temperatures and under conditions suitable for its application to non-inert surfaces such as those found on agricultural products would be advantageous as a means of sanitizing fruits, tubers, and vegetables in situ in the storage facility while simultaneously sanitizing the storage facility itself. Also, a method of generating peroxyacetic acid vapor using atmospheric air would have similar utility since many of the agricultural and other facilities where the process might be used lack ready access to sterile compressed air or other sterile gasses.

SUMMARY OF THE INVENTION

Recently, it has been discovered that a disinfecting aqueous solution of peroxyacetic acid ranging from 10,000 PPM to 42,000 PPM that is: 1) Admixed with trace amounts of water softening or chelating agents; 2) Repeatedly heated to form a super-heated vapor with temperature above about 250° C.; 3) Cooled to a temperature below about 55° C. as it settles through room temperature atmospheric air; and, 4) Applied for periods of time in excess of 40 minutes yields at least three useful improvements over the prior art, including: 1) Obviating the need for a source of sterile air; 2) Allowing the use of well or tap water when preparing the diluted aqueous peroxyacetic acid solution; and, 3) Exhibiting heightened antimicrobial activity when the vapor is applied at low temperatures (i.e. less than about 55° C.). This new process allows peroxyacetic acid vapor to be generated without the need for a source of laboratory grade sterile water or sterile air or other gas and to be safely applied to both inert solid surfaces and non-inert surfaces such as those found on agricultural products thus allowing users to sanitize fruits, tubers, and vegetables in situ in the storage facility while simultaneously sanitizing the storage facility itself.

Therefore, the goals of the present method are to: 1) Provide a method for preparing a suitable aqueous peracetic acid solution for vaporization at high temperature; 2) Provide a means for using well or tap water and atmospheric air to create the necessary vapor thus obviating the need for a separate supply of sterile water and sterile air or some other sterile gas; and, 3) Provide a method of using this vapor at or about room temperature to sanitize various inert solid surfaces and non-inert surfaces such as those found on agricultural products thus allowing the simultaneous sanitization of: a) Fruits, tubers, and vegetables in situ in the storage facility; and, b) The storage facility itself.

DETAILED DESCRIPTION OF THE INVENTION

According to the present method, a commercially available aqueous mixture of 5% peracetic acid (PAA) is diluted with well water or ordinary tap water to make a solution comprised of between 1:4 to 4:1 parts 5% peroxyacetic acid to water. Commercial 5% peroxyacetic acid solutions are usually comprised of peroxyacetic acid and stabilizing amounts of hydrogen peroxide and acetic acid and added water in the approximate ratio of 5:20:10:65. Additional components may be added, including stabilizers such as phosphonic acid, sequestriants such as dipicolinic acid, as well as other ingredients such as protic acid catalyzing agents (e.g., sulfuric acid, nitric acid, and phosphoric acid), and surfactants (e.g., non-ionic laurylates and sorbitans). Those having skill in the art will readily recognize that peroxyacetic acid is commercially available in a wide range of concentrations including, for example, 3%, 5%, 10%, and 15%. While the preferred embodiment of the present method comprehends using a 5% solution, it should be readily apparent to those having skill in the art that equivalent dilutions can be made using peroxyacetic acid in other concentrations and that all such dilutions are incorporated in the spirit and scope of this disclosure.

When diluted with water to a range between 1:4 to 4:1 parts 5% peroxyacetic acid to water, an aqueous peracetic acid solution with a concentration of peroxyacetic acid in the range of about 10,000 PPM to about 42,000 PPM is formed. As mentioned above, commercial peroxyacetic acid solutions ordinarily have a significant fraction of acetic acid added as a stabilizing agent. Nevertheless, to further stabilize the peroxyacetic acid during vaporization, an additional measure of acetic acid (less than about 10% by weight) may be added to the aqueous peracetic acid solution. Also, trace amounts of chelating agents or water softening agents such as disodium phosphate may be added to this mixture to retard mineral scale buildup in the atomizing device and thus aid in vaporization of the mixture.

The mixture is pressure fed into an atomizing device wherein the mixture is mechanically introduced as a high-pressure mist or spray into ambient temperature atmospheric air. This forms a cool mist or spray. This cool mist or spray is heated and vaporized by repeatedly passing the mist or spray in close proximity to one or more a heating elements integral to the atomizing device. Alternately, the mixture may be directly introduced as a liquid into a circulating superheated air stream. In this case the rate at which the liquid is introduced into the superheated air stream is controlled such that the liquid vaporizes instantly. In both cases the mixture further decomposes as it repeatedly circulates and a superheated vapor containing molecular water, peracetic acid, and any admixed acetic acid or chelating agents is produced at user selectable temperatures above about 250° C. By elevating the temperature of the vapor to such high levels well water or ordinary tap water may be used when preparing the diluted solution and compressed or uncompressed atmospheric air may be used in lieu of sterile air or some other sterile gas. It will be readily apparent that ambient air may be substituted all or in part with sterile air, nitrogen, carbon dioxide, Noble gases, and various mixtures thereof.

The peroxyacetic acid thermally dissociates via two main reactions:

$$CH_3CO_2\text{—}OH \rightarrow CH_3CO_2^- + OH^- \rightarrow CH_3 + CO_2 + OH^- \quad \text{(i)}$$

$$CH_3CO_2\text{—}OH \rightarrow CH_3COOH + O \quad \text{(ii)}$$

The intermediate acetic acid decomposes via a third independent reaction:

$$CH_3COOH \rightarrow (CH_3CO)_2O + C_2H_2O + H_2O \quad \text{(iii)}$$

After exiting the atomizing device, the superheated vapor cools as it settles through the air. In use, the atomizing device is located a sufficient distance from the material to be treated such that the temperature of the vapor as it impinges on the surface of the material is below about 55° C. Ordinarily, the vapor would be applied at a temperature approximating the ambient temperature in the storage facility and this can range between about 10° C. and about 25° C. By allowing the vapor to cool to this temperature, the user may safely apply the vapor to both inert solid surfaces and the non-inert surfaces of agricultural products. Because antimicrobial hydroxyl ions and elemental oxygen were in relatively high concentration in this vapor when it was generated, a significant fraction of these antimicrobial substances impinge on the surface to be sanitized in significant concentrations. When applied for periods of time ranging from 40 minutes to 8 hours, this process serves to sanitize exposed surfaces and kill virtually all bacteria, bacterial spores, fungi, protozoa, algae, and viruses on both stored agricultural products and on the surfaces of the storage facilities in which the agricultural products are stored.

Suitable surfaces include, but are not limited to, the exterior surfaces of agricultural products such as vegetables and fruits, surgical and technical instruments, surgical treatment suites and hospital rooms, agricultural and commercial storage containers and buildings, agricultural production facilities such as dairies, and so on.

The process works best in an environment with an initial relative humidity above about 30%. As a result, in low humidity environments, the relative humidity at the application point must be artificially raised into the proper range.

The efficacy of the sanitizing regime of preferred embodiment of the present method is demonstrated by means of the following example:

EXAMPLE 1

A dense suspension of conidia from a 2-week old colony of *Penicillin digitatum* cultured at 24° C. on potato dextrose agar was collected on a fine-haired brush and immediately applied onto one side of each of 18 craft wood sticks, 10 cm in length and 0.5 cm wide. These were dried in air one day before use. Six each of these craft wood sticks were attached to the walls of three identical commercial citrus storage rooms. The craft wood sticks were distributed at equal intervals along both walls and at the back of each room and placed at low and high levels from the floor. Half were placed about 50 cm from the floor and half were placed about 200 cm from the floor. All three rooms were humidified for about 1 hour such that the relative humidity in all three rooms was not less than about 85% and the temperature was in the range of about 20° to about 22° C. The volume of each room was approximately 36,500 ft$^3$.

One room was designated as the Control Room, one room was designated as Treatment Room 1, and the third room was designated as Treatment Room 2. Treatment Rooms 1 and 2 were to be treated with 3.5 fluid ounces per 1000 $ft^3$ of Jet-Ag™ formulation peroxyacetic acid (hydrogen peroxide 26.5% and peroxyacetic acid 4.9%). The Control Room was left untreated. By using identical commercial facilities, both the potency and homogeneity of the distribution of the materials within the existing commercial rooms could be assessed under practical conditions in a single series of tests.

In Treatment Room 1, about 1 U.S. gallon of Jet-Ag™ was added to about 3 U.S. gallons of tap water. The equipment used in the application of the aqueous Jet-Ag™ solution was a proprietary thermo-fogger (GroupAg LLC, Rexburg, Id.) that uses repeated heating cycles to generate a superheated vapor with a temperature in the range of about 260° C. to about 280° C. which settles through ambient air to create a low temperature fog (between about 10° C. and about 25° C.) with very small droplet sizes (<0.5 microns). This technique is known as "low water volume thermo-fogging" (LWVTF) and comports with the teachings of the present method.

In Treatment Room 2, about 1 U.S. gallon of Jet-Ag™ was added to about 100 U.S.

gallons of sterile humidification water. The equipment used in the application of the aqueous Jet-Ag™ solution was a proprietary air-assisted fogger (Fruit Growers Supply Company (dba FGS Packing Services), Exeter, Calif.) that uses compressed-air liquid dispersion nozzles placed in a 1 m diameter fan to disperse a fog with larger droplet sizes (10 to 15 microns). This technique is known as "high water volume air assisted fogging" (HWVAAF) and represents a commonly used means of distributing chemical fogs in agricultural applications.

All three rooms were sealed. In both Treatment Room 1 and 2, delivery of the entire disinfectant volume timed to occur over a 3 to 4 hour period and the fog was allowed to remain in each room until it dissipated. After 24 hours, each room was opened, aerated for about 1 hour and the craft wood sticks were retrieved. Each craft wood stick was placed in a sterile test tube, a small measured amount of 0.1% weight/volume Triton TX-100 non-ionic surfactant was added, each craft wood stick was vortexed briefly, and 20 μl containing 200 to 500 conidia was placed on potato dextrose agar. After incubating 18 hours at 20° C., the number of germinated conidia were counted using a compound microscope at 200 power.

The following data were observed:

| Room | Disinfectant Method | Disinfectant | Germination % (±σ) | Range % |
|---|---|---|---|---|
| Control | None | None | 93.3 (±5.5) | 85.0-98.0 |
| Treatment Room 1 | LWVTF | Jet-Ag ™ | 0.0 (±0.0) | 0.0-0.0 |
| Treatment Room 2 | HWVAAF | Jet-Ag ™ | 2.0 (±2.6) | 0.0-8.3 |

The Jet-Ag™ formulation of peracetic acid was effective and practical for sanitation purposes in both Treatment Room 1 and 2. However, the low water volume thermo-fogging method practiced in accordance with the teachings of the present method was significantly more effective than the more commonly practiced high water volume air assisted atomizer fogging method. Moreover, the low water volume thermo-fogging method practiced in accordance with the teachings of the present method required significantly less water and obviated the need for a sterile humidification water supply.

What is claimed is:

1. A method of sterilizing agricultural products in situ, said method comprising the steps of:

a) Heating a diluted aqueous solution of peracetic acid containing at least about 10,000 ppm of peracetic acid to form a superheated peracetic acid vapor in ambient air;

b) Cooling said superheated peracetic acid vapor to a temperature below about 55° C.;

c) Contacting this cooled peracetic acid vapor with the agricultural products in situ to be sterilized.

2. The method of claim 1 wherein said diluted aqueous solution of peracetic acid contains peracetic acid in a concentration greater than about 10,000 PPM and less than about 42,000 PPM.

3. The method of claim 1 wherein said diluted aqueous solution of peracetic acid is diluted using water selected from the group comprising sterile water, tap water, and well water.

4. The method of claim 1 wherein less than about 10% by weight of acetic acid is added to said diluted aqueous solution of peracetic acid.

5. The method of claim 1 wherein said diluted aqueous solution of peracetic acid is further treated with a water softening agent.

6. The method of claim 1 wherein contact between the cooled peracetic acid vapor and the material to be sterilized occurs in an environment with an initial relative humidity of greater than about 30%.

7. The method of claim 1 wherein contact between the peracetic acid vapor and the material to be sterilized is maintained for a period greater than about 40 minutes.

* * * * *